United States Patent [19]

Friemel et al.

[11] Patent Number: 4,503,032

[45] Date of Patent: Mar. 5, 1985

[54] HYDROGEN-PHOSPHIDE RELEASING COMPOSITIONS AND THEIR USE

[75] Inventors: Wolfgang Friemel, Heppenheim; Reiner Ehret, Weinheim, both of Fed. Rep. of Germany

[73] Assignee: Dr. Werner Freyberg Chemische Fabrik Delitia Nachf, Laudenbach, Fed. Rep. of Germany

[21] Appl. No.: 436,769

[22] Filed: Oct. 26, 1982

Related U.S. Application Data

[63] Continuation of Ser. No. 215,586, Dec. 11, 1980, abandoned.

[30] Foreign Application Priority Data

Dec. 18, 1979 [DE] Fed. Rep. of Germany ....... 2950999

[51] Int. Cl.$^3$ .................... A01N 25/18; A01N 59/26; A01N 59/16
[52] U.S. Cl. ..................................... 424/40; 424/128; 424/145
[58] Field of Search .......................... 424/40, 128, 145

[56] References Cited

U.S. PATENT DOCUMENTS

| | | | |
|---|---|---|---|
| 2,826,486 | 3/1958 | Hülter | 424/128 |
| 3,132,067 | 5/1964 | Rauscher | 424/128 |
| 3,372,088 | 3/1968 | Werner | 424/128 |
| 3,917,823 | 11/1975 | Kapp | 424/128 |
| 4,213,967 | 7/1980 | Werner | 424/128 |
| 4,376,112 | 3/1983 | Miller | 424/128 |

FOREIGN PATENT DOCUMENTS

| | | | |
|---|---|---|---|
| 1143053 | 1/1963 | Fed. Rep. of Germany | |
| 1569514 | 6/1980 | United Kingdom | 424/128 |

*Primary Examiner*—Delbert R. Phillips
*Assistant Examiner*—F. T. Moezie
*Attorney, Agent, or Firm*—Millen & White

[57] ABSTRACT

A phosphine releasing composition suitable for use as a pest control agent comprising a mixture of aluminium phosphide, zinc or a zinc compound and a source of ammonia or ammonium ion, can be produced by mixing the components. The zinc or zinc compound in combination with the ammonia or ammonium ion protects the compositions when exposed to water vapor or liquid water against auto-ignition.

26 Claims, No Drawings

HYDROGEN-PHOSPHIDE RELEASING COMPOSITIONS AND THEIR USE

This is a continuation of application Ser. No. 215,586 filed Dec. 11, 1980, now abandoned.

BACKGROUND OF THE INVENTION

The present invention relates to hydrogen phosphide-releasing compositions, especially to pest control agents, comprising aluminium phosphide.

For purposes of pest control and protection of stored agricultural commodities preparations based on hydrolysable phosphides of alkaline earth and/or earth metals such as calcium, magnesium or aluminium phosphide are employed to an increasing extent. These are caused by atmospheric humidity or the moisture content of stored commodities to decompose into highly toxic phosphine and inert oxides/hydroxides. The liberated phosphine may auto-ignite under certain unfavorable conditions, for which reason special expedients are necessary to permit the application safely and without hazard. In addition it is generally desired to so regulate the hydrolysis rate of the phosphides that the fumigation workers are not exposed unnecessarily to toxic gas concentrations.

Substances which thermally decompose to liberate $NH_3$ and/or $CO_2$ such as ammonium bicarbonate, ammonium carbonate, ammonium carbamate etc. have been used successfully for suppressing the tendency to auto-ignite of phosphine formed hydrolytically from phosphides. More recently other inhibitors have been described which even in low concentrations inhibit or retard the spontaneous reaction between phosphine and atmospheric oxygen. It is also known to admix to the phosphide readily volatile organic substances, the heat of evaporation of which causes the phosphide particles to be surrounded by a cooled zone, thereby preventing heat accumulation which might result in ignition of the phosphine.

These measures have very little or no effect on the violent rate of formation of the phosphine which results when the metal phosphide comes into contact with liquid water. To suppress this reaction with liquid water it has been proposed to hydrophobise the phosphides or phosphide particles. Paraffins, waxes, stearates, silicones, synthetic resins etc. have been described as hydrophobing agents. See, e.g., U.S. Pat. Nos. 3,132,067; 3,372,088; Fed. Rep. of Germany DOS No. 27 005 228; and U.S. application Ser. No. 964,410, filed Nov. 28, 1978 now abandoned, whose disclosure is incorporated herein by reference, and the references cited therein. It is also known that the individual phosphide particles or groups of particles are coated with a water-repellent dense coating which is claimed to prevent hydrolysis such that a bursting substance is added which is said to burst open the coating and thus trigger the reaction with moisture after a time delay.

It was furthermore known to depress the reactivity of metal phosphides against liquid water in pest control agents by blocking the hydrophilic centers of the phosphides with water-insoluble metal soaps, in particular stearates. The expressly described purpose of this procedure was the abolition of previously known auto-ignition inhibitors, in particular ammonia salts such as ammonium carbamate. This procedure was equally effective for calcium phosphide, magnesium phosphide as well as aluminium phosphide. For various commercial and practical reasons aluminium stearate (and to a lesser extent magnesium stearate) were selected as the preferred blocking agent and even used on a commercial scale in certain countries by the present applicant.

Practical experience and experiments have shown that the above described teaching may at the most serve to maintain a reasonable control over the hydrolysis of alkaline earth and earth metal phosphides caused by atmospheric humidity. If phosphide containing pest control agents prepared according to the state of the art, are contacted with liquid water, as may very well happen accidentally in practice, it is found that, depending on the ratio of water/preparation more or less severe steam generation and temperature rises to values even exceeding 100° may result, demonstrating that the reaction cannot be controlled adequately. Under such conditions the admixed protecting agents are volatilised very rapidly so that they do not yield an adequate protective effect. Moreover, the measured reaction temperatures are at least in part within the range of the ignition temperature of phosphine which according to the literature is approximately 100° C. In the experiments, the oxidation of the phosphine, i.e., the formation of $P_2O_5$, smoke and sometimes even spontaneous ignition may be observed. It would be highly desirable—and this is an object of this invention—to mitigate this safety risk which should not be under-estimated in the practical context, and nevertheless to provide an easily manufactured and safely applied pest control agent based on hydrolyzable aluminium phosphide.

SUMMARY OF THE INVENTION

The present invention provides a hydrogen-phosphide releasing composition comprising aluminium phosphide in admixture with an amount effective to inhibit aut-ignition in the presence of humidity, more particularly humid air or liquid water of a mixture of (a) zinc or a zinc compound compatible with the aluminium phosphide and (b) a source of ammonia or ammonium ions.

DETAILED DISCUSSION

The hydrogen phosphide releasing agent preferably compises the aluminium phosphide in finely particulate form, intimately mixed with the remaining ingredients of the aforesaid combination.

The composition which optionally contains conventional additives can be advantageously used as a pest control agent.

In that case the composition may be made up in a conventional manner for that purpose, e.g. in the form of pellets, tablets or sachets (filled with the composition in powder or granulate form) representing standardised dosage units as conventionally used in the art, e.g. for the direct application in warehouses, silos, storage bins or similar closed spaces containing, e.g. agricultural commodities or for the control of burrowing animals. The procedures suitable for pest control using the claimed compositions can be the same as are normally employed with prior art compositions.

It was found that the decomposition of this pest control agent in accordance with the invention brought about by liquid water proceeds extremely slowly. In the hydrolysis experiments conducted not a single case of steam or even worse, $P_2O_5$ formation was observed and the maximum reaction temperatures were in the region of 50° C. Moreover, it made little or no difference whether the formulations were used in loose or compacted form.

Not even the ratio of the preparation to water had any serious influence on the progress of the hydrolysis. However, the decomposition of formulations according to the invention brought about by atmospheric moisture, i.e. the gas generating characteristics are not affected by the addition of the zinc compounds.

Accordingly, it was found possible for the first time to prevent reliably in the case of an aluminium phosphide containing pest control agent the ignition temperature being even approached. This provides protection against an ignition of the hydrogen phosphide taking place even when liquid water is permitted to contact the pest control agent, e.g., due to careless use or malpractice.

Surprisingly, not only metallic zinc in powder form and zinc oxide, but also salt-like zinc compounds which contain zinc cations are effective to inhibit hydrolysis. The nature of the anion was found to be immaterial, although obviously a person skilled in the art would avoid anions which are strong oxidising agents or which in the context of practical use are likely to produce undesirable corrosion or toxicity problems, e.g., in the residue from the spent preparations. Preferably the quantities employed amount to about 0.1–5% by weight of the composition, which composition comprises aluminimum phosphide, an $NH_3$ or $[NH_4]+$ generating substance and, where appropriate, an hydrophobing agent. Higher proportions are possible, but do not result in any further improvement. In selecting a suitable zinc compound care should obviously be taken to ensure that it is anhydrous and will not adversely affect the physical and chemical characteristics of the phosphide. Zinc oxide, inorganic salts of zinc and weak or strong mono or polybasic acids, e.g. basic zinc carbonate, zinc sulphate or zinc borate, and organic zinc salts, e.g., salts of organic fatty acids, e.g. zinc soaps, especially zinc stearate, are particularly suitable. These zinc compounds are advantageously employed in finely comminuted form; their effectiveness increases as the specific surface thereof is increased.

Essential for an inventive effect of the zinc compounds is the presence in the composition of a source of ammonia or ammonium ions, e.g., a substance which is decomposable under conditions under which the aluminium phosphide is hydrolyzed to yield $NH_3$, e.g. thermally, such as for example, ammonium bicarbonate, ammonium carbonate, ammonium carbamate, or which is capable of dissociating, e.g. in the presence of water, to yield ammonium ions, e.g. ammonium biphosphate and ammonium chloride, etc. If such a substance is lacking, the zinc compounds lack the desired effect. The amount of added substance yielding $NH_3$ or $[NH_4]+$ is in the range of 10 to 50%, preferably 15 to 30% based on the total amount of the composition. Appreciable variations above this range can be tolerated. Substances which yield $NH_3$ by decomposition are of course also sources of ammonium ion in the presence of liquid water. Apparently the ammonium ion (in a manner not yet understood), plays a part in the protective mechanism which suppresses violent reactions with liquid water. Surprisingly, the zinc compounds or the metallic zinc only influence the hydrolytic reaction of aluminium phosphide with water and they exert this influence only if ammonia or ammonium ion generating compounds are present. The reaction of other metal phosphides conventionally employed in pest control, namely magnesium and calcium phosphide, is not effected to any material extent.

It is a further surprising fact that the hydrolysis retarding effect of the zinc compounds or zinc powder is observed even in the absence of the normally used hydrophobing agents. However, since conventional hydrophobing agents, such as for example, paraffins, waxes, stearates, etc. besides their hydrophobic effect also act as lubricants and binding agents in the context of making compressed bodies, their use in making compacted pest control compositions of this invention is advantageous.

The aluminium phosphide can be, and in practice generally will be, of a technical grade as is produced in a kiln by reaction of pure aluminium powder with red phosphorus. The product, hereinafter referred to as technical aluminium phosphide, is substantially composed of aluminium phosphide and aluminium oxide. The AlP content is preferably about 75 to 90%, more particularly 85%.

The technical aluminium phosphide is ground to a powder composed of particles ranging from fine dust up to 2000$\mu$, preferably not more than 20% being larger than 1000$\mu$ or smaller than 50$\mu$. For practical purposes it is particularly important that the zinc compounds or zinc powder in accordance with the invention exercise their hydrolysis regulating effect even by simple admixture to the remaining components of the formulation. In the case of using organic soaps of zinc it may moreover be advantageous if they are admixed with the remaining components as a solution in a suitable anhydrous solvent, e.g. chlorinated hydrocarbons. After the evaporation of the solvent, a homogeneous mixture is present which can be immediately subjected to further processing, e.g. tableting or granulating.

Formulations of this invention can be used either in loose form, e.g. granules or powders, in suitable containers such as sachets of fabric, paper or fibrous nonwoven fabrics, or in the form of pressed bodies, such as pellets or tablets, according to the methods which are conventional in pest control using phosphide containing pesticides. Also suitable are formulations which have been converted into granulate form by means of suitable binding agents. Suitable binding agents are natural and synthetic polymers which are soluble in low boiling anhydrous organic solvents so as to leave after the evaporation thereof a polymer film on the individual particles or particle groups. For purposes of the present invention, it is immaterial whether the polymers besides being soluble in organic solvents are also soluble in water. However, when it is desired to achieve a good granulation effect without impairing the wettability of the composition, e.g. for purposes of complete hydrolysis of spent residues of such compositions, a water-soluble non-water repellent polymer is preferred.

The protective effect afforded by the combination of zinc (or zinc compound) and ammonia and/or ammonium ion on the aluminium phosphide is so great that for the first time it is now possible even to intentionally contact the aluminium phosphide composition with liquid water, e.g. for the purpose of generating phosphine gas substantially free of the higher homologues of phosphine, e.g. for laboratory or other chemical use or for pest control purposes.

Accordingly, the present invention according to one of its aspects also provides a use of the composition as set out herein, namely a method of generating phosphine gas which comprises exposing a composition as herein set out, to water, thereby hydrolysing the aluminium phosphide with the formation of phosphine gas. The water may be in vapor form (as in the prior art fumigation methods employing metal phosphide preparations) or it may be employed in liquid form, e.g. in a generator vessel which can be of quite simple construction.

For pest control purposes, the phosphine gas generated may be introduced immediately into and maintained in an environment infested with pests to be eradicated.

To be on the safe side even under extreme conditions, it is sometimes advantageous to add to the pest control agent small quantities of other ignition inhibiting substances, many of which are known in the prior art, e.g., certain alkyl and alkenyl substituted aromatic hydrocarbons having, e.g., a benzene nucleus substituted with 2-5 alkyl or alkenyl substituents or a naphthalene nucleus substituted with 2-3 alkyl or alkenyl substituents can be used. See, e.g., U.S. Pat. No. 4,213,967, whose disclosure is incorporated herein by reference.

Further precautions in the context of hydrolysing the preparations with liquid water are directed to minimizing heat build-up. For this purpose the aluminium phosphide composition in granulate, pellet or tablet form is fed little by little into a generating vessel containing water, e.g. with known metering devices, preferably over a period spread out over a major part of the total fumigation period. This procedure (which can be fully automatized in manners requiring no detailed description) can simultaneously serve to maintain in the space a phosphine concentration range known to be optimum for the particular fumigation procedure (which may vary depending on climate, nature of the pests, nature of the commodity, nature of the space and time available for the fumigation).

In the context of fumigating a warehouse, silo, storage bin or similar closed space, e.g. containing agricultural commodities to be fumigated, the air may be withdrawn by suction from such space into a phosphine generating vessel and recycled, together with phosphine into the space. The recycling may take place through one or more pipes which preferably extend some distance away from the walls into the space interior.

If comparatively large quantities of the composition have to be hydrolysed in a relatively short time it may be advisable to subject the water in the generator vessel to cooling.

The following examples serve to elucidate the invention without limiting the same. All proportions, unless otherwise stated, are given in parts by weight (mass). The technical aluminium phosphide used in the examples is of conventional grade (85% AlP), ground to a powder substantially in the particle range 50–2000μ and typically having the following particle size distribution:

>1000μ: 10%
>500μ: 30%
>100μ: 85%
<100μ: 15%, and a loose bulk density of 0.7 g/cm$^3$.

EXAMPLE 1

70 parts technical aluminium phosphide, 25 parts ammonium carbamate and 3 parts stearin were intimately mixed. The basic mixture was divided, one half being pressed directly into moulded bodies of 3 g each, the other half being similarly pressed after the admixture thereto of 2% of a commercial grade of zinc stearate having a bulk density after shaking of 115 g/l. Lots of 10 tablets each of each composition were subjected in a 250 ml glass beaker to a drenching with 30 ml H$_2$O at 20° C. The temperature rise caused by the hydrolysis was measured by means of an electrical thermometer.

Whereas the temperature maximum of the formulation containing zinc stearate was to about 37° C., the basic mixture attained a maximum value of about 93° C.

EXAMPLE 2

70 Parts technical aluminium phosphide were mixed at 120° C. with 4 parts hard paraffin according to DAB 6.* After cooling to room temperature the hydrophobised AlP was mixed with 26 parts ammonium carbamate and one half of this mixture was pressed directly into moulded bodies of 3 g each (A). The other half of the mixture was similarly pressed into tablets of 3 g each after the addition thereto of 0.5 parts of a zinc oxide having a BET surface area of 10 m$^2$/g. Subsequently all moulded bodies were subjected to a brief thermal treatment (1 hour, 70° C. in a closed vessel) to increase the hydrophobic effect.

*German Pharmacopeia Vol. 6

Lots of 10 tablets each of each composition were hydrolyzed in a 400 ml glass beaker with 30 ml H$_2$O. In the case of the formulation according to the invention, the maximum reaction temperature was about 31° C., whereas the tablets without zinc oxide attained 105° C. In the latter case P$_2$O$_5$ smoke was observed.

EXAMPLE 3

60 Parts technical aluminum phosphide, 35 parts urea and 3 parts aluminium stearate were intimately mixed with 10 parts of a 20% suspension of zinc stearate according to example 1 in dichloromethane (B). A second mixture was produced in which the 20 parts urea were replaced by ammonium carbamate. The mixture containing ammonium carbamate during the hydrolysis experienced only very moderate reaction, whilst the phosphine formed by the hydrolysis from the other formulation ignited spontaneously. The reaction temperature measured prior to the ignition reached about 107° C.

EXAMPLE 4

70 Parts technical aluminium phosphide were treated at 140° C. for one hour with 0.5 parts of a methyl hydrogen polysiloxane in the absence of air. After the silicone had been cured and after cooling to room temperature 15 parts ammonium chloride and 14 parts urea and 0.5 parts finely comminuted zinc borate were added.

Lots respectively composed of 10 tablets of 3 g pressed from this mixture and 10 tablets of a mixture of 70 parts technical aluminium phosphide, 26 parts ammonium carbamate and 4 parts hard paraffin DAB 6 were drenched at 35° C. room temperature in a 250 ml glass beaker with 30 ml H$_2$O at 35° C. The maximum reaction temperature in the case of the formulation according to the invention was about 39° C. The control tablets attained a maximum value of 92° C. with steam development.

EXAMPLE 5

Batches of 10 each of the tablets according to the invention and of the control tablets according to example 4 were exposed to air for 3 hours. This was followed by a hydrolysis experiment as in example 4. The tablets according to the invention reacted very slowly and attained a maximum reaction temperature of 38° C. The phosphine gas evolved by the control tablets achieved auto-ignition after a brief reaction period.

EXAMPLE 6

A mixture of 70 parts technical aluminium phosphide, 15 parts ammonium chloride, 14,8 parts urea and 0,2 parts of a zinc oxide according to example 2 were pressed into pellets of 0.6 g each. 50 g of these tablets were subjected to reaction in a 1 liter beaker with 50 ml H$_2$O. The hydrolysis proceeded extremely slowly and the maximum reaction temperature was about 23° C.

Tablets were hydrolyzed as a control which had the same composition except that they contained no zinc oxide (C). Shortly after the start of hydrolysis, the phosphine generated ignited.

EXAMPLE 7

70.5 parts of an aluminium phosphide treated in accordance with example 4, 19.3 parts urea, 10 parts ammonium carbamate and 0.2 parts zinc oxide (BET surface area 10 m$^2$ g) were mixed intimately in the absence of air and subsequently pressed into tablets of 3 g each.

Tablets were used as a control which were composed of a mixture of 70.5 parts siliconised aluminium phosphide, 19.5 parts urea and 10 parts ammonium carbamate. (D). 10 tablets of each batch were hydrolysed in a 250 ml glass beaker with 30 ml H$_2$O. The reaction temperature of the formulation containing zinc oxide attained a maximum temperature of 35° C. The control tablets attained 105° C. with a formation of P$_2$O$_5$ smoke.

EXAMPLE 8

70 parts technical aluminium phosphide, 15 parts ammonium carbamate, 13.5 parts urea, 0.5 parts zinc oxide were mixed intimately and subsequently sprayed with 10 parts of a 10% solution of polyvinyl pyrrolidone in dichloromethane. After the evaporation of the solvent, the formulation took the form of a fine granulate. 50 g each of this granulate and of an otherwise identical granulate lacking the omission of the zinc oxide were subjected to reaction with 50 ml H$_2$O in a 400 ml glass beaker.

The reaction of the granulate without zinc oxide proceeded rapidly and violently with the formation of P$_2$O$_5$ smoke. The formulation in accordance with the invention reacted very slowly and only attained a maximum reaction temperature of 37° C. in spite of the absence of any hydrophobing agent.

EXAMPLE 9

70 parts technical aluminium phosphide, 20 parts ammonium carbamate, 7 parts urea and 3 parts aluminium stearate were intimately mixed in the absence of air.

This mixture was divided, one half being pressed directly into moulded bodies of 3 g each and the other half was so pressed after the addition of two parts zinc powder (commercially known as Zn dust).

These pressed tablets were subjected to the following hydrolysis tests: batches of 10 tablets were each drenched in a 400 ml glass beaker with 20 ml water and the temperature rise during the hydrolysis was measured. The temperature maximum of the zinc containing tablets was in the region of 34° C., whereas the tablets without zinc attained 94° C. and formed P$_2$O$_5$ smoke.

EXAMPLE 10

70 parts of a technical aluminum phosphide, 15 parts ammonium carbamate, 12 parts urea and 3 parts stearic acid were intimately mixed in the absence of air. One half thereof was directly pressed into tablets of 6 g each and the other half was so pressed after the addition of 2 parts zinc sulphate. A hydrolysis experiment (according to example 9) was then conducted, in which the reaction of the pest control bodies containing zinc sulphate proceeded very gently, the maximum temperature being at 33° C. The control pressed bodies reacted considerably more violently with the formation of P$_2$O$_5$ smoke.

EXAMPLE 11

Tablets were produced according to example 10 in which the zinc sulphate was replaced by basic zinc carbonate.

These tablets reacted very slowly with H$_2$O, whereas the corresponding tablets free of zinc salt experienced a violent reaction and evolved P$_2$O$_5$ smoke.

TABLE 1

| Formulation according to example | Composition in parts by weight | Temperature after | | | | | T max. (min) |
|---|---|---|---|---|---|---|---|
| | | 5 min | 10 min | 15 min | 30 min | 60 min | |
| 1 | 70 Alp, 25 AC, 3 stearin, 2 Zn—stearate | 22 | 24 | 26 | 34 | 32 | 37° (55 min) |
| 2 | 70 Alp, 26 AC, 4 Paraffin 0.5 ZnO | 22 | 23 | 25 | 27,5 | 28 | 31° (95 min) |
| 3 | 60 Alp, 20 AC, 15 urea, 3 Al stearate, 2 Zn stearate | 21 | 23.5 | 26 | 29 | 34 | 36° (45 min) |
| 4 | 70 Alp, 15 NH$_4$Cl, 14 urea, 0.5 H—siloxane, 0.5 Zn—borate | 21 | 22 | 23,5 | 26 | 26,5 | 26,5° (55 min) |
| 6 | 70 Alp, 15 NH$_4$Cl, 14.8 urea, 0.2 ZnO | 20 | 20 | 20,5 | 21,5 | 22 | 23° (75 min) |
| 7 | 70 Alp, 10 AC, 19.3 urea, 0.5 H-siloxane, 0.2 ZnO | 22 | 24 | 27 | 33 | 34 | 35° (75 min) |

AlP = aluminium phosphide of technical grade
AC = ammonium carbamate

| Control Batch | Composition in parts by weight | Temperature after | | | | T max. (min) |
|---|---|---|---|---|---|---|
| | | 5 min | 10 min | 15 min | 30 min | |
| A | 70 Alp, 26 AC, Paraffin | 25 | 31 | 62 | 80 | 105° (20 min) |
| B | 60 Alp, 35 urea, 3 Al—stearate 2 Zn—stearate | 25 | 43 | 104 | | 107° (17 min) |
| C | 70 Alp, 15 NH$_4$Cl, 15 urea | 28 | 74 | 97 | | 114° (13 min) |
| D | 70 Alp, 10 AC, 19.5 urea. | 26 | 37 | 63 | 76 | 105° (24 min) |

TABLE 1-continued

Temperature pattern of the hydrolysis of 10 tablets each with 30 ml H₂O 0.5 H—siloxane AlP - technical aluminium phosphide, AC - ammonium carbonate, Paraffin - hard paraffin DAB 6
H—siloxane - hydrogenpolymethylsiloxane The tablets according to examples 1 to 6 were subjected to the following experiment:

3 tablets each were exposed in a gas chamber of ½ m² capacity at 20° C. and approximately 70% relative air humidity, and the amount of $PH_3$ liberated was determined by means of Draeger tubes at fixed intervals. It was found that in spite of extremely retarded reaction with liquid water, the reaction with atmospheric moisture was not impeded.

The results are tabulated in table 2. The samples are denoted as in table 1.

TABLE 2

| Formulation according to example | PH₃ generation | | | | | | | |
|---|---|---|---|---|---|---|---|---|
| | 30 min | 1 h | 2 h | 3 h | 4 h | 5 h | 6 h | 24 h |
| 1 | 80 | 120 | 240 | 370 | 490 | 560 | 680 | 2400 |
| 2 | 80 | 180 | 280 | 320 | 400 | 540 | 680 | 2350 |
| 3 | 40 | 90 | 180 | 290 | 370 | 510 | 610 | 2400 |
| 4 | 60 | 160 | 280 | 430 | 600 | 670 | 790 | 2350 |
| 6 | 90 | 200 | 300 | 450 | 550 | 700 | 790 | 2400 |
| A | 70 | 180 | 250 | 350 | 400 | 520 | 700 | 2400 |
| B | 80 | 180 | 270 | 350 | 410 | 500 | 590 | 2200 |
| C | 90 | 190 | 310 | 450 | 630 | 710 | 780 | 2350 |

Table 2 shows clearly that the addition of the zinc compounds in accordance with the invention does not interfere with the decomposition of the aluminium phosphide due to atmospheric moisture. In this context it should be noted that the formulation according to example 3 contains 60% aluminium phosphide.

The present invention makes possible the provision of pest control agents on the basis of hydrolyzable aluminium phosphide which while retaining the desired gas generation characteristics in accordance with the existing state of the art, contributes substantially to improved safety against fire in the practical application of these pest control agents.

What is claimed is:

1. In a hydrogen-phosphide releasing pesticidal composition comprising particulate aluminum phosphide in intimate admixture with an auto-ignition inhibitor which comprises a source of ammonia or ammonium ions which is decomposable to yield $NH_3$ under conditions under which the aluminum phosphide is hydrolyzed or which is capable of dissociating in the presence of water to yield ammonium ions and which is effective to inhibit auto-ignition in the presence of humidity but which is ineffective to inhibit auto-ignition in the presence of liquid water, the improvement wherein the composition further comprises an amount effective to inhibit auto-ignition in the presence of liquid water of zinc or a zinc compound which is compatible with the aluminum phosphide.

2. A composition according to claim 1 containing an organic zinc compound.

3. A composition according to claim 2 wherein the zinc compound is a zinc soap.

4. A composition according to claim 3 wherein the zinc soap is zinc stearate.

5. A composition according to claim 1 containing an inorganic zinc compound.

6. A composition according to claim 5 wherein the inorganic zinc compound is zinc oxide.

7. A composition according to claim 6 wherein the inorganic zinc compound is zinc hydroxide-carbonate, zinc sulfate or zinc borate.

8. A composition according to claim 1 containing metallic zinc powder.

9. A composition according to claim 1 containing an ammonium salt as the source of ammonia or ammonium ion.

10. A composition according to claim 1 in the form of a powder or granules.

11. A composition according to claim 1 in the form of tablets or pellets.

12. A composition according to claim 1 comprising a hydrophobing agent.

13. A composition according to claim 1 containing at least about 0.1% by weight thereof of the zinc or zinc compound.

14. A composition according to claim 13 containing 0.2 to 3% by weight thereof of the zinc or zinc compound.

15. A composition according to claim 14 containing at least about 10% by weight thereof of the source of ammonia or ammonium ion.

16. A composition according to claim 15 containing 15 to 30% by weight thereof of the source of ammonia or ammonium ion.

17. A composition according to claim 1 containing about 30 to 75% by weight thereof of technical grade aluminum phosphide.

18. A composition according to claim 1 in the form of a powder containing 0.2 to 3% by weight thereof of the zinc or zinc compound; 15 to 30% by weight thereof of the source of ammonia or ammonium ion; and about 30 to 75% by weight thereof of technical grade aluminim phosphide.

19. A composition according to claim 1 in the form of tablets or pellets containing 0.2 to 3% by weight thereof of the zinc or zinc compound; 15 to 30% by weight thereof of the source of ammonia or ammonium ion; and about 30 to 75% by weight thereof of technical grade aluminum phosphide.

20. A composition according to claim 1 in the form of a granulate containing 0.2 to 3% by weight thereof of the zinc or zinc compound; 15 to 30% by weight thereof of the source of ammonia or ammonium ion; and about 30 to 75% by weight thereof of technical grade aluminum phosphide.

21. A composition according to claim 1 containing about 10 to 50% by weight thereof of ammonium chloride, ammonium carbonate, ammonium carbamate or ammonium bicarbonate as the source of ammonia or ammonium ions; about 0.1 to 5% by weight thereof of zinc powder, zinc oxide, zinc hydroxidecarbonate, a zinc salt of an inorganic mono- or polybasic acid or a zinc salt of an organic acid; and about 30 to 75% by weight thereof of technical grade aluminum phosphide.

22. A method of generating phosphine gas from aluminum phosphide without risk of auto-ignition which comprises exposing a composition of claim 1 to liquid water or to water vapor.

23. A method according to claim 22 wherein the water is in the form of water vapor.

24. A method according to claim 23 wherein the composition is exposed to the water vapor in an environment susceptible to infestation by pests.

25. A method according to claim 22 wherein the phosphide is exposed to water in liquid form.

26. A method according to claim 25 wherein the phosphine gas thus produced is introduced into and maintained by an environment susceptible to infestation by pests.

* * * * *